United States Patent [19]
Bendel et al.

[11] Patent Number: 5,350,419
[45] Date of Patent: Sep. 27, 1994

[54] CARDIAC PACING LEAD

[75] Inventors: Lee P. Bendel, Lebanon; Timothy A. Sardelis, Somerset; Leon K. Stungurys, Middlesex; Thomas A. Astarita, Flemington, all of N.J.

[73] Assignee: Ethicon, Inc., Somerville, N.J.

[21] Appl. No.: 947,207

[22] Filed: Sep. 18, 1992

[51] Int. Cl.$^5$ .............................. A61N 1/05
[52] U.S. Cl. ..................... 607/132; 607/119; 128/642
[58] Field of Search .............. 128/642, 132, 119

[56] References Cited
U.S. PATENT DOCUMENTS

4,341,226  7/1982  Peters ........................... 128/784
4,566,467  1/1986  Dettaan ......................... 128/784
4,633,880  1/1987  Osypka et al. ................. 128/785
5,086,787  2/1992  Grandjean et al. ............. 128/786

*Primary Examiner*—William E. Kamm
*Assistant Examiner*—Scott M. Getzow
*Attorney, Agent, or Firm*—Emil Richard Skula

[57] ABSTRACT

A novel cardiac pacing lead. The pacing lead has a conductive wire comprising a single filament of a low modulus metal. A surgical needle is mounted to a distal end of the wire and an electrode needle is mounted to the proximal end of the wire. An integral anchor is formed in a distal, uninsulated section of the wire for anchoring the pacing lead in heart muscle. The wire has a "hand" similar to multifilament wires.

44 Claims, 6 Drawing Sheets

CARDIAC PACING LEAD

TECHNICAL FIELD

The field of art to which this invention relates is surgical electrode leads, more particularly, cardiac pacing and monitoring leads.

BACKGROUND OF THE INVENTION

Cardiac surgical procedures are well known and the associated surgical techniques have progressed to the point where the risk to the patient has been greatly minimized. At the conclusion of cardiac surgery, it is typical for the surgeon to implant temporary pacing leads in the myocardium of the atria or ventricles of the cardiac patient's heart. The primary purpose of the temporary pacing leads is to provide a means for pacing the atria and ventricles. The pacing leads also provide a means for recording myocardial electrograms.

Conventional temporary pacing leads typically consist of a conductive wire lead and a surgical needle for implantation in the myocardium. The needle typically has a distal piercing end and a proximal end which is attached to the distal end of the wire lead. An electrode needle is typically attached to the proximal end of the wire lead. The wire lead typically has an insulated section and a distal conductive section where the insulation has been removed. The distal conductive section is implanted in the cardiac muscle. The electrode needle is typically pushed through the thoracic cavity wall ( i.e., from the interior to the exterior ) and the insulated section of the wire lead is partially pulled through. The electrode needle is connected to conventional pacing and monitoring equipment.

Conventional wire leads are typically made from multi-filament conducting materials such as stainless steel. The leads are insulated with bio-compatible polymer coatings . It is important that the wire have a feel to the surgeon similar to that of a conventional suture. This is known in this art as "hand".

Conventional cardiac pacing leads are typically used in the following manner. Initially, the surgeon inserts the curved surgical needle into the myocardium. Next, the surgeon pushes the needle through and out of the myocardium such that a portion of the uninsulated, distal conductive section of the pacing wire is implanted in a needle pathway formed in the myocardium by the surgical needle. The surgical needle is then cut from the pacing wire, and, the pacing wire is optionally anchored to the heart with a suture. Then, the surgeon pushes the scored electrode needle, connected to the proximal end of the pacing wire, out through the wall of the thoracic cavity so that the electrode needle and a length of the insulated section of electrode lead wire are positioned external to the chest of the patient. The electrode needle is then broken at the score line and inserted into the appropriate receptacle of a conventional electronic pacing and monitoring device. Typically, the leads are removed from the patient, after the patient has been stabilized, in the following manner. The surgeon disconnects the electrode needle from the monitoring/pacing device. The surgeon then grasps the external section of the pacing wire and pulls it by applying traction( i.e., an axial, rearward force), thereby pulling the lead from the myocardium and out through the chest wall.

It is known that pacing leads must have certain characteristics. First of all, the lead wire must be very flexible and resistant to fatigue failure resulting from repeated flexing cycles. It can be appreciated that a cardiac patient may have the pacing leads in place for periods of time up to and exceeding two or three weeks. During that time normal voluntary and involuntary movements by the patient( such as heartbeats, respiration and ambulation) will result in repetitive flexing of the wire lead. Another requirement for cardiac pacing leads is that the implanted myocardial lead must remain in place when subjected to typical stress and strain caused by typical patient movement and activities. However, the implanted lead must be easily withdrawn from the myocardium by the application of an axial force, i.e., traction, to the wire lead. Yet another requirement is that the pacing wire be constructed of material having a low electrical resistance. Additionally, the cardiac pacing leads should be easy to manufacture. A further requirement is that the cardiac leads must be sufficiently flexible to provide the surgeon with a "hand" similar to that of a conventional suture. Still another requirement of a pacing lead is biocompatability such that the pacing lead is corrosion resistant, nontoxic, and nonallergenic.

Conventional cardiac pacing leads are known to have deficiencies. Typically, conventional pacing leads use a multi-conductor(filament) wire having an outer electrically insulating coating such as the multi-filament stainless steel sutures disclosed in U.S. Pat. No. 3,125,095. A multi-filament pacing wire, although providing the required "hand", flexibility and resistance to fatigue, also allows the growth of tissue into the interstices of the wire in sections where the outer insulation has been removed. This tissue ingrowth complicates and may impeded removal of the pacing lead from the heart. Furthermore, from a manufacturing perspective, multi-filament wire is difficult to work with. For example, it is difficult to strip all of the insulation coating from a multi-filament wire using conventional wire stripping equipment. A residue of insulation in the interstices between the filaments is typically left behind. Any residual insulation may adversely affect pacing and monitoring. In addition, when using a multi-filament wire , it is necessary to simultaneously cut the wire and weld the ends of the strands. Cutting and welding must be done at the same time in order to prevent unraveling. It is known that when cut and welded ends are inserted into surgical needles for mounting it is possible for there to be deficient electrical contact between the cut and welded end of the wire and the needle. This poor electrical contact may be caused by oxidation or poor physical configuration resulting from the cutting and welding step.

The use of a single filament wire would eliminate some of these disadvantages. However, although single filament wires made from conventional metals may have been used for cardiac pacing leads, they have the disadvantages of not having the proper "hand" and of being susceptible to fatigue fracture or failure.

Another disadvantage of conventional pacing leads is that the pacing lead must somehow be anchored in the myocardium. This is frequently done by suturing the electrical lead in place to the heart muscle using conventional suture materials. The additional sutures required for anchoring may increase the trauma to the heart and may complicate removal of the pacing lead. Another method of anchoring is the use of helical suture structures affixed distally to the pacing lead. For example, U.S. Pat. No. 4,341,226 discloses a temporary lead for cardiac pacing or monitoring purposes. The lead has a curved needle having an attached surgical suture with a proximal helix molded into the suture immediately distal to the pacing lead. The helical suture and pacing lead are placed within the myocardium and the helical suture serves to anchor the lead within the myocardium. The helical anchor suture is typically nonconductive and this type of cardiac pacing lead typically has less conductive surface in contact with the myocardium. Yet another method of anchoring a pacing wire involves inserting a pacing wire which is completely insulated into the myocardium. An excess length is pulled through the myocardium. The surgeon the strips the insulation off from opposite sides of a section of the wire forming two small wings of stripped insulation material. The surgeon then applies traction on the lead, thereby pulling the excess lead back into the myocardium until the stripped section of wire is in the myocardium. The wings of insulation remain exterior to the myocardium and serve as an anchor. The stripping is typically done with a scalpel blade. This method of anchoring has many disadvantages including the additional time necessary to perform the wire stripping procedure as well as danger to the patient and surgeon while attempting to strip insulation from a wire lead with a scalpel.

There are disadvantages to either of these methods of securing the pacing wire to the myocardium in that removal of the pacing wire may cause significant trauma to the myocardium. In addition, pacing leads such as those disclosed in U.S. Pat. No. 4,341,226 have a conductive section which is larger in diameter than the pathway formed by the surgical needle in the myocardium. This results in additional stress or trauma to the myocardium when the conductive section is inserted or removed.

What is needed in this art are new pacing leads which overcome the disadvantages of conventional pacing leads.

SUMMARY OF THE INVENTION

Therefore, it is an object of the present invention to provide a pacing lead having a single conductor wire which has the flexibility of a multi-conductor wire pacing lead.

It is a further object of the present invention to provide a pacing lead which has a "hand" similar to conventional sutures.

It is yet a further object of the present invention to provide a pacing lead which has an integral anchoring means that is less traumatic than the anchoring means used for conventional pacing wire leads.

It is yet a further object of the present invention to provide a pacing lead having a conductive wire which has a maximum diameter which is less than or equal to the maximum dimension of the surgical needle.

It is yet another object of the present invention to have a pacing lead with an anchor wherein the anchor is conductive.

Accordingly, a novel cardiac pacing lead is disclosed. The pacing lead comprises a conductive wire comprising a biocompatible, low modulus metal. The wire has a proximal end and a distal end. The wire comprises a single filament conductor. A surgical needle is conductively attached to the distal end of said wire for insertion into and through heart muscle. An electrode needle is conductively attached to the proximal end of the wire for connection to an external pacing or monitoring device. An integral anchor is formed into the distal end of the wire for anchoring the lead in the myocardium.

Yet another aspect of the present invention is a cardiac pacing wire. The wire comprises a single filament conductor. The wire has a proximal end and a distal end. The wire comprises a single filament conductor. A surgical needle may be conductively attached to the distal end of said wire for insertion into and through heart muscle. An electrode needle may be conductively attached to the proximal end of the wire for connection to an external pacing or monitoring device. An integral anchor is formed into the distal end of the wire for anchoring the lead in the myocardium of a mammal.

Another aspect of the present invention is a method of cardiac pacing or monitoring using the previously-described cardiac pacing lead. The method comprises inserting the surgical needle and the distal end of the conductive wire, including the anchor means, into the myocardial heart muscle of a mammal. Then, inserting the electrode needle through the chest wall of the mammal along with the proximal end of the conductive wire means and inserting the electrode means into a cardiac pacing and/or monitoring device. And, then pacing and/or monitoring the heart of the mammal.

Other features and advantages of the invention will become more apparent from the following description and accompanying drawings.

BEST MODE FOR CARRYING OUT THE INVENTION

Figure 1:
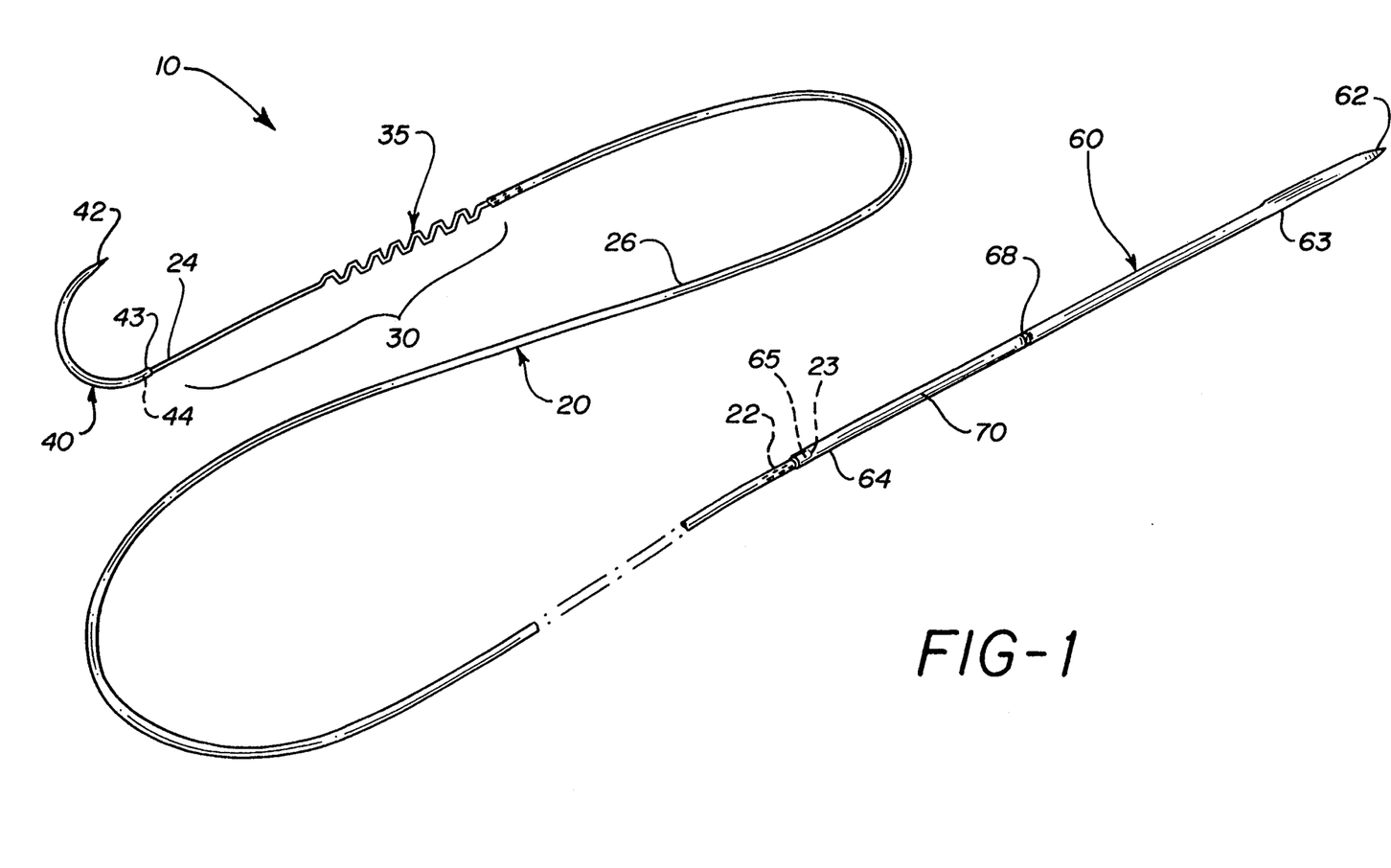
FIG. 1 is a perspective view of the cardiac pacing wire of the present invention.

The cardiac pacing lead 10 of the present invention is illustrated in FIGS. 1-5 and FIGS. 7A-F. Referring to FIG. 1, the cardiac pacing lead 10 is seen to have a single filament, electrically conductive, low modulus wire 20 having proximal end 22 and distal end 24. The wire 20 also has distal tip 25 and proximal tip 23. The conductive, low modulus wire 20 is seen to have electrically insulating coating 26. A portion of the insulating coating 26 is seen to be removed from a distal section 30 of the conductive wire 20. At least part of section 30 of the conductive wire 20 will be in electrical contact with the myocardium for transmitting and receiving electrical signals. Formed into section 30 is the integral anchor means 35.

Figure 5:
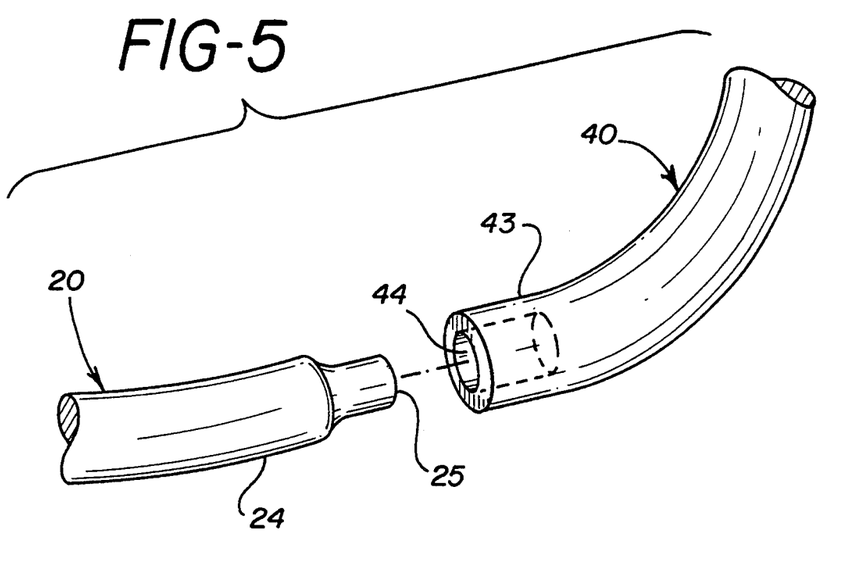
FIG. 5 is a perspective view of an embodiment of the wire showing the connection of the surgical needle and the reduced distal end of the pacing wire.

Surgical needle 40 is seen to have distal point 42 and proximal mounting cavity 44 (as seen in FIG.5) for mounting the distal tip 25 of the conductive wire 20. The distal tip 25 of conductive wire 20 is inserted into the mounting cavity 44 of needle 40 and mounted in a conventional manner such as swaging, welding, brazing, bonding with a medically approved bonding agent such as epoxy (e.g., a conductive epoxy) and shrink fitting and the like. Referring to FIG. 5, it is seen that the distal tip 25 may be of a lesser diameter than the wire 20 to facilitate mounting in cavity 44. It is desirable, although not necessary, that the connection between tip 25 and the needle 40 in cavity 44 be sufficient to provide electrical conduction between the wire 20 and the needle 40.

The needle 40 is typically a conventional curved myocardial surgical needle having a conventional distal piercing point and a conventional proximal end 43 with a cavity 44 suitable for receiving a suture or a wire. The diameter of the wire 20 will be less than or equal to the maximum trans-axial dimension (e.g., diameter) of the needle 40. The needle 40 is preferably made from a conductive metal conventionally used to manufacture surgical needles such as martensitic stainless steel, maraging stainless steel, plated carbon steel, cold drawn austenitic stainless steel and the like. However, if one were willing to accept any disadvantages which may be attendant, if any, the needle 40 could be made of nonmetallic conducting materials having the requisite mechanical characteristics for use as a surgical needle.

The electrode needle 60 is attached to the proximal tip 23 of the conductive wire 20. The needle 60 is typically a conventional electrode needle and has a straight configuration having a proximal point 62 and a distal end 64 containing mounting cavity 65. The electrode needle 60 has scoreline 68 centrally located about the circumference of the needle. The scoreline 68 will be of sufficient depth so that the proximal end 63 of the needle 60 may be easily broken off leaving an electrode portion 70 for insertion into an electronic cardiac pacing/monitoring instrument 80. Distal end 64 of the needle 60 has mounting cavity 65 for receiving proximal tip 23 of wire 20. The tip 23 must be mounted such that it is in sufficient mechanical engagement with needle 60 in cavity 65 to provide effective electrical contact. Conventional mounting methods may be used including swaging, soldering, brazing and the like. The needle 60 will be made from conventional materials such as martensitic stainless steel, maraging stainless steel, plated carbon steel, cold drawn austenitic stainless steel and the like having sufficient conductivity to effectively transmit low level electrical signals. Electrode needles are disclosed in U.S. Pat. No. 4,010,756 which is incorporated by reference.

The conductive wire 20 will be made from a single filament, low modulus metal having the requisite electrical properties, biocompatibility properties and mechanical properties. The term low modulus as used herein is defined to mean a modulus of elasticity in tension of less than $2.0 \times 10^6$ pounds per square inch (psi). The term metal is defined to include metal alloys. The metals useful to form the conductive wires 20 of the present invention will typically have the following characteristics: "hand" low modulus of elasticity, good fatigue resistance and biocompatiblity including corrosion resistance. Examples of low modulus metals which can be used include the various shape memory alloys such as Nitinol, gold-cadmium alloys, titanium-niobium alloys, nickel-titanium-copper alloys, nickel-titanium-platinum alloys and nickel-titanium-palladium alloys. The alloys will typically have the following compositions: Nickel-titanium with 50% nickel or less, Nickel-titanium-copper alloys with about 5 to about 20% copper, Nickel-titanium-platinum alloys with above about 15% platinum, and nickel-platinum-palladium alloys with above about 18% palladium. It is preferred to use the nickel-titanium alloys which are often referred to as shape memory effect alloys.

The low modulus, single filament, conductive wire 20 will have an electrical conductivity sufficient to prevent attenuation of cardiac pacing signals or myocardial electrical activity signals. The electrical resistivity of the material will typically be about 50 to about 200 microhm-cm, more typically about 60 to about 120 microhm-cm, and preferably about 80 to about 100 microhm-cm. The conductive wire 20 will have sufficient mechanical strength and resistance to fatigue to effectively prevent fatigue failure or tensile failure of the wire 20 while implanted in a cardiac patient. In addition, the wire 20 will have sufficient yield strength to prevent the anchor means 35 from straightening out in the tissue pathway created in the myocardium by the surgical needle 40. Typically, the wire 20 will have a yield strength of less than about 40,000 pounds per square inch, more typically less than about 30,000 pounds per square inch, and preferably less than about 20,000 pounds per square inch. The wire 20 will typically have a U.S.P. size of 1/0, 2/0 or 3/0 as indicated in the U.S. Pharmacopeia which is incorporated by reference.

As seen in FIG. 1, the wire 20 has an electrically insulative, polymer coating 26 sufficient to effectively prevent conduction through the coating. Preferably, the coating 26 will have a thickness of about 2.0 mils to about 50.0 mils, more typically about 2.0 mils to about 25.0 mils, and preferably about 3.0 mils to about 8.0 mils. The coating 26 will contain conventional biocompatible polymers and copolymers including polyethylene, polypropylene, Teflon ® (polytetrafluoroethylene), fluorinated ethylenepolypropylene, and equivalents thereof. The insulative coating 26 will be applied in conventional manners such as spraying, rolling, brushing, extruding and the like. It is also possible to use a shrink-type tube of insulation material applied concentrically about the wire and actuated by application of sufficient energy to shrink and engage the wire 20 to form coating 26.

Figure 2:
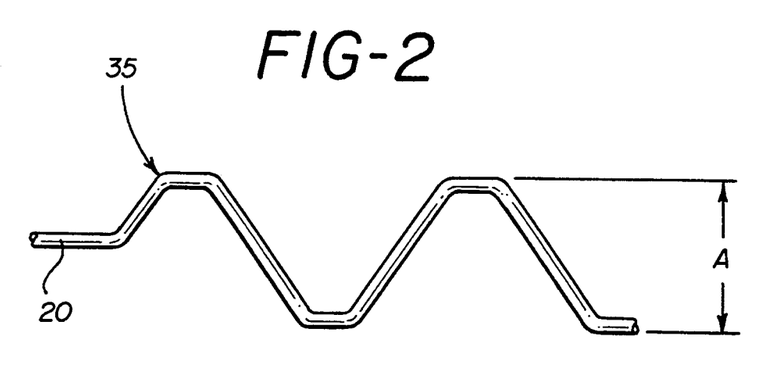
FIG. 2 is a plan view of the anchor means of the cardiac pacing wire of the present invention as used in Example 1.
Figure 3:
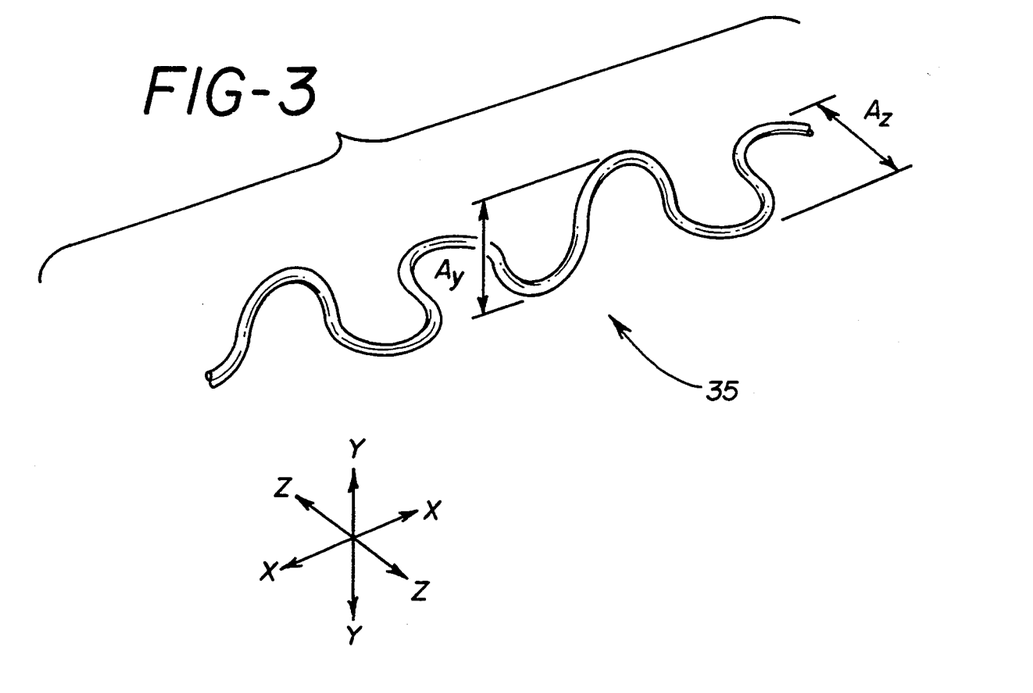
FIG. 3 is a perspective view of a three-dimensional embodiment of an anchor means in a cardiac pacing wire of the present invention.

The anchor section 35 of the pacing lead 10 is typically formed in the following manner. A section of the insulation coating 26 is removed from a distal section of wire 20, using a conventional wire stripping apparatus, to produce the uninsulated section 30. The section 30 of the wire 20 is fed into a conventional press apparatus having dies, and, is compressed in the apparatus using sufficient force to permanently deform the section 30 into a desired anchor configuration or wave form. In one method, the anchor 35 (as seen in FIG. 2) is made by rolling or pressing section 30 between two rotatably mounted, meshing gears. Any conventional process may be used to form anchor 35 including mechanical processes such as that described above, wherein the form or configuration of the anchor 35 is set into the section 30. Several configurations for the anchor 35 are illustrated in FIGS. 7A-7F. The configurations which can be used for anchor 35 include any configurations effective to produce sufficient anchoring of the pacing lead 10 in the myocardium without disengaging from the needle pathway in response to typical patient movements. The shapes include any conventional waveform including sinusoidal, square, saw tooth, and gear, either full wave or half wave or combinations thereof, for example, as seen in FIGS. 7A–F. The waves will typically repeat with a desired periodicity and will have a sufficient amplitude to provide effective anchoring in the myocardium. The anchors may have two-dimensional or three-dimensional configurations (as shown in FIG. 3) wherein the waveforms or shapes are rotated periodically about the longitudinal axis of the wire. Although waveform shapes are preferred, the anchor 35 may have a variety of different shapes which are effective to anchor the wire 20 in the myocardium, including a helix.

The force to remove the anchor 35 from a needle pathway in heart muscle will vary with the size and configuration of the anchor as well as the length and size of the needle pathway. The force will typically be about 17 grams to about 1000 grams, more typically about 100 grams to about 300 grams, and preferably about 150 grams to about 300 grams.

A typical amplitude "A" for the anchor 35 is seen in FIG. 2. The amplitude A is defined to be the sum of the maximum distance above and below the longitudinal center line of the wire 20. The amplitude A of anchor 35 is sufficient to effectively anchor the pacing lead 10 in the myocardium. Typically, amplitude A is about 15 mils to about 75 mils, more typically about 20 mils to about 60 mils, and preferably about 25 mils to about 50 mils. If the anchor 35 has a waveform configuration, the frequency will be sufficient to provide effective retention in the heart muscle. Typically, the frequency will be about 1 cycle per inch to about 20 cycles per inch, more typically about 5 cycles per inch to about 15 cycles per inch; and preferably about 5 cycles per inch to about 10 cycles per inch.

The length of the anchor 35 will vary depending upon such variables including the type of patient and the desired withdrawal force. The length of anchor 35 will be sufficient to effectively prevent inadvertent withdrawal from the cardiac muscle by providing effective retention in a needle pathway in cardiac muscle. Typically the length of the anchor 35 will be about 0.5 inches to about 3.0 inches, more typically about 0.75 inches to about 2.0 inches, and preferably about 1.0 inches to about 1.5 inches.

Figure 6:
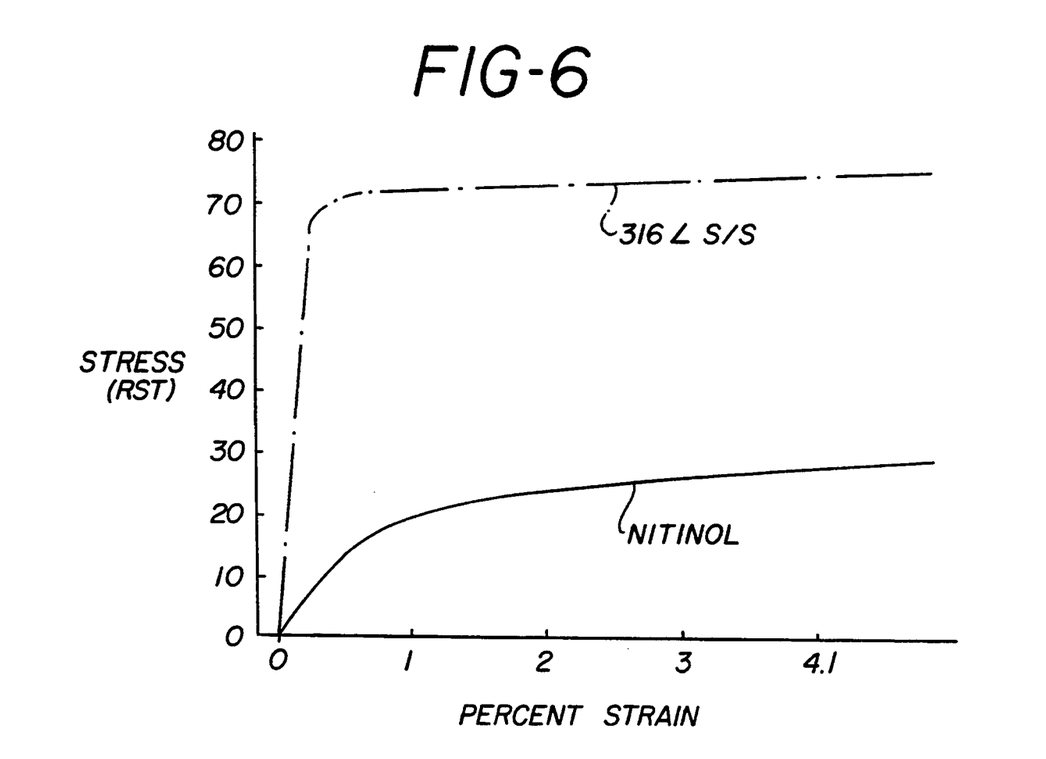
FIG. 6 is a graph illustrating a comparison of the tensile curves for Nitinol and Type 316 stainless steel.
Figure 7A:
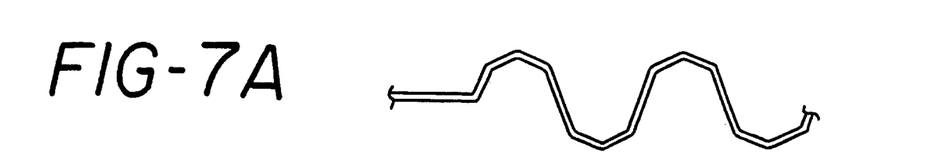
FIGS. 7A-7F illustrate various anchor shapes for the pacing wire of the present invention.
Figure 7B:
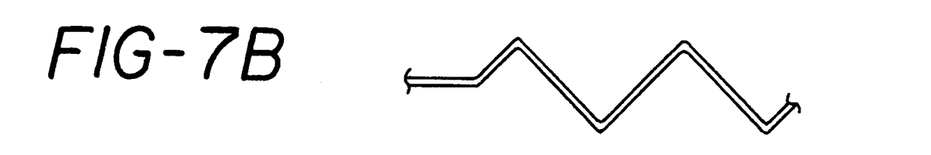
Figure 7C:
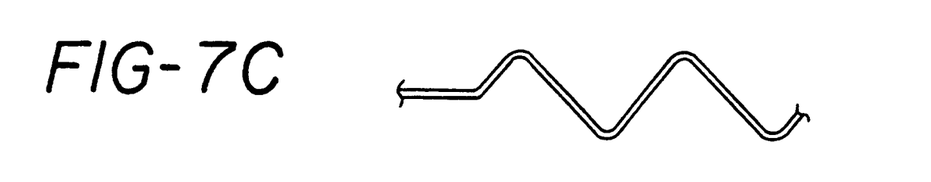
Figure 7D:
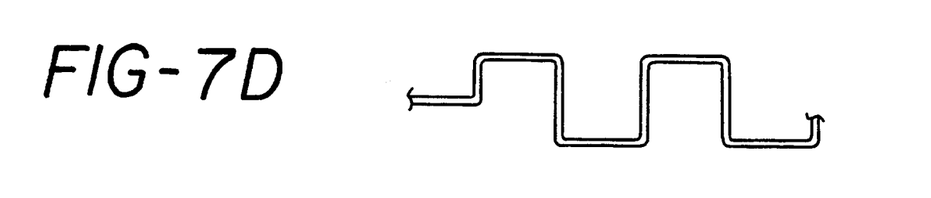
Figure 7E:
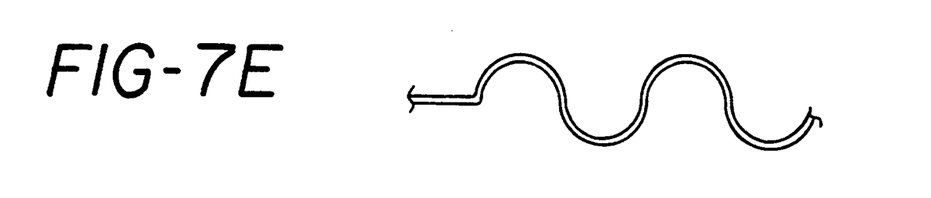
Figure 7F:
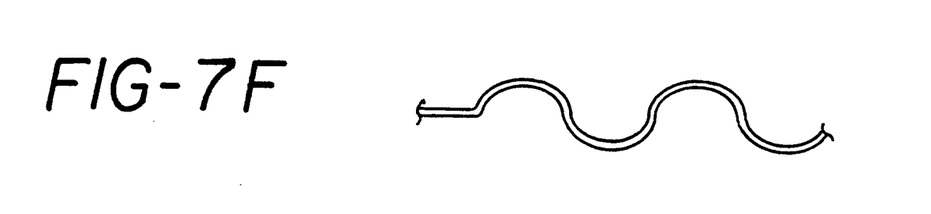

In order to have the proper hand, the cardiac pacing lead 20 must have a wire section 20 which has a feel or stiffness (i.e., "hand") similar to a conventional surgical suture. Conventional surgical sutures are typically made from materials such as polypropylene, dacron-polyester and absorbable polymeric materials. The modulus of elasticity of the conventional suture materials ranges from about 100,000 psi to about 2,000,000 psi. Therefore, the modulus of elasticity of the metals suitable to make the wire 20 will be sufficient to effectively provide a hand comparable to conventional sutures. Typically, the modulus of elasticity will be about $1 \times 10^6$ psi to about $2 \times 10^6$ psi, more typically about $1.2 \times 10^6$ psi to about $1.8 \times 10^6$ psi, and preferably about $1.4 \times 10^6$ psi to about $1.6 \times 10^6$ psi. A diagram of stress versus percent strain is illustrated in FIG. 6 showing curves for Type 316-L stainless steel and Nitinol, respectively. Nitinol, which has a "hand" similar to conventional sutures, is seen to undergo percentage increases in strain at significantly lower stress values than stainless steel. This behavior is characteristic of low modulus materials having the desired "hand".

Figure 4A:
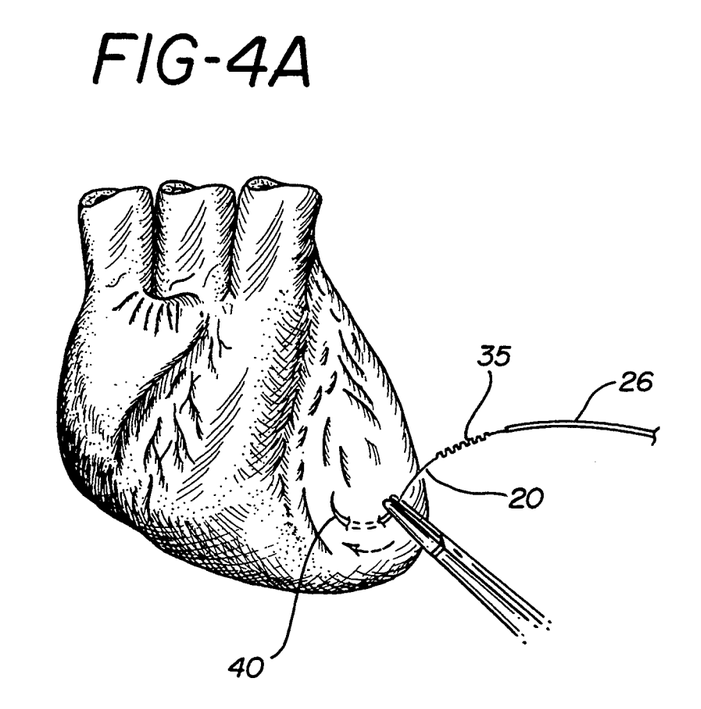
FIGS. 4A-C are sequential views illustrating the cardiac pacing wire of the present invention emplaced into a mammalian heart.
Figure 4B:
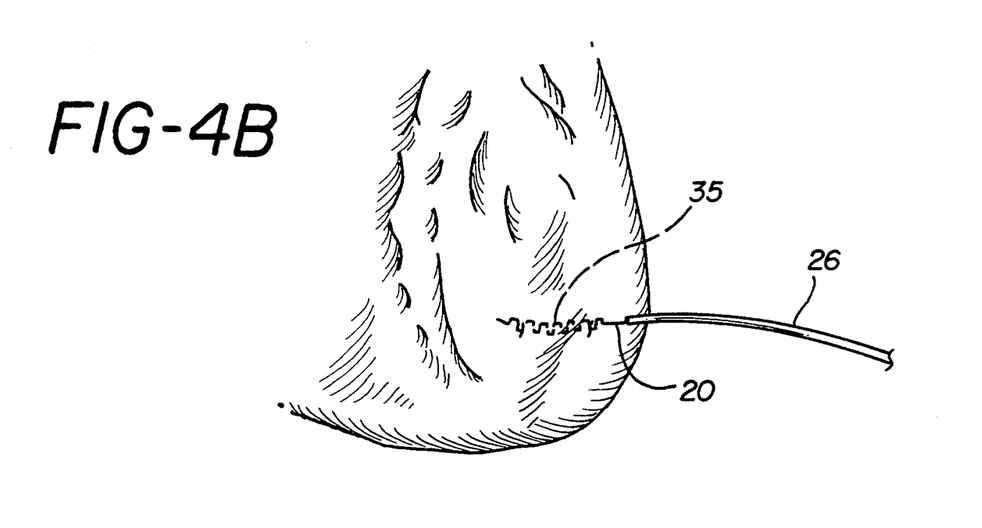
Figure 4C:
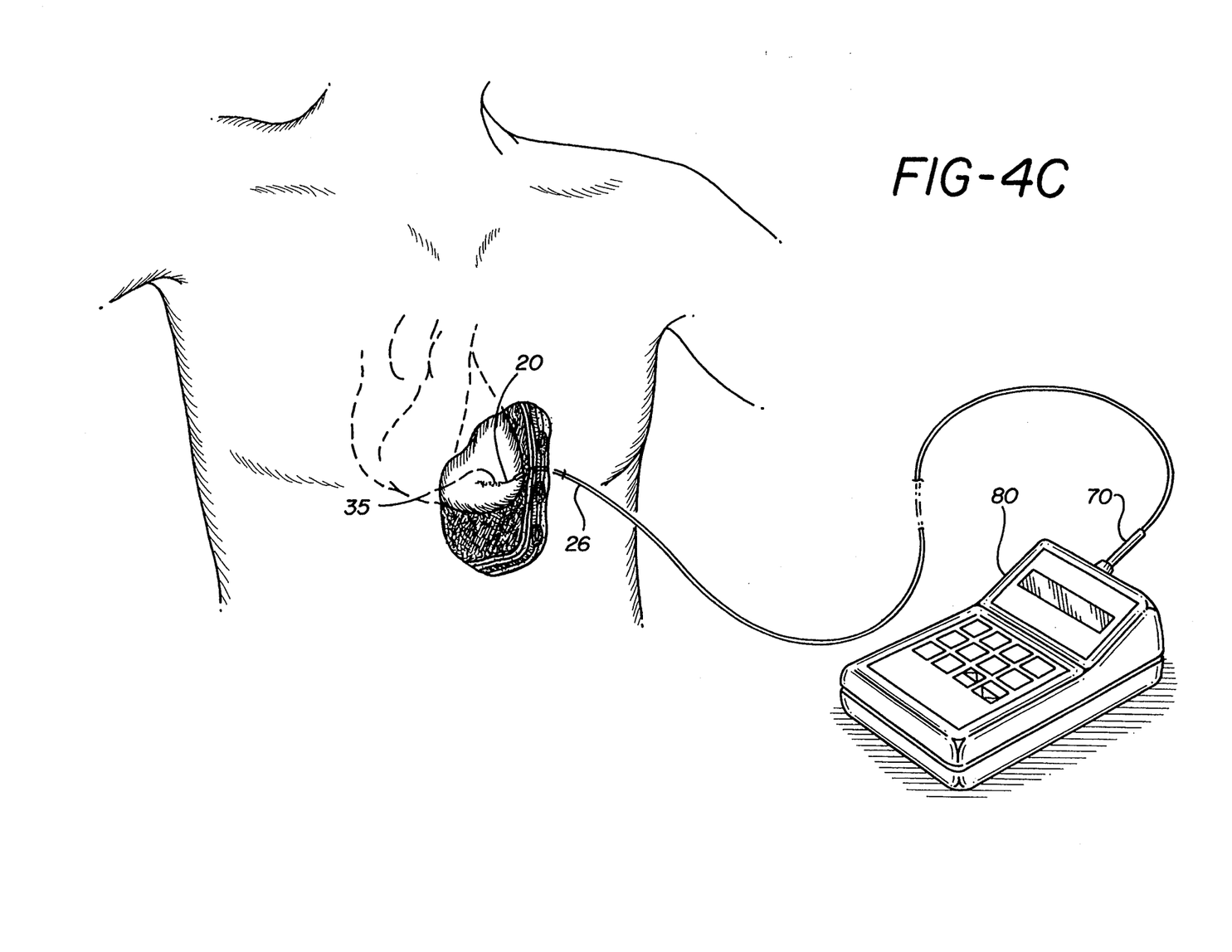

The cardiac pacing leads 10 of the present invention are typically used in the following manner, as illustrated in FIGS. 4A–4C. After a conventional cardiac surgical procedure has been performed, the needle 40 of the pacing lead 10 is inserted into and through the pericardium of the patient's atria or ventricles and the needle is pushed through until the tip 42 is exposed (thereby creating a needle pathway in the heart muscle). The surgeon then grasps the tip 42 with a surgical grasping instrument and pulls the needle through the heart muscle until the anchor section 35 of the conductive wire 20 is sufficiently in place in the heart muscle to effectively anchor the pacing lead 10. Next, the needle 40 is cut from the distal end 24 of the wire 20. Then, the surgeon pushes the electrode needle 60 outward from the interior of the thoracic cavity through the intercostal spaces in the patient's thoracic cavity wall until the distal end 63 of the needle 60 protrudes through the exterior of the thoracic cavity wall. The surgeon then grasps the end 63 of the needle with a conventional needle grasper or holder and pulls the needle 60 and an insulated, proximal of the wire 20 through the thoracic cavity wall. Next, the surgeon breaks the end 63 off of the needle 60 by grasping the proximal end 63 and the distal end 64 of the needle 60 and applying a bending moment about the score line 68. Then, the physician inserts the electrode portion 70 of the needle 60 into a receptacle on a cardiac pacing/monitoring instrument 80. The cardiac pacing lead 10 then serves as an electrical connection between the patient's pericardium and the cardiac pacing/monitoring instrument 80. The patient's heart is monitored or paced by the cardiac pacing/monitoring instrument 80 through the cardiac pacing lead 10.

After the patient has stabilized and recuperated sufficiently to no longer require cardiac monitoring and pacing, the pacing lead 10 is removed by initially disconnecting the electrode section 70 of the electrode needle 60 from the cardiac pacing/monitoring equipment. Then, the surgeon applies traction by applying an axial proximal force on the cardiac pacing lead 10 and removes the anchor 32 and the wire 20 by pulling the assembly out through the patient's chest wall.

The following examples are illustrative of the principles and practice of the present invention although not limited thereto.

EXAMPLE 1

Nitinol wire 20 having a diameter of 15 mil was used to manufacture cardiac pacing leads 10. The composition of the Nitinol was 49.5% Ni and 50.5% Ti. A distal section 30 of insulation 26 was removed using conventional wire stripping equipment. An anchor 35 was formed in the wire 20 by running the distal section 30 of the wire 20 through a set of rotating gears. The anchor 35 had a wave form configuration as seen in FIG. 2. A conventional surgical needle 40 was swaged to the distal tip 25 of the wire 20. The leads 10 were implanted into a porcine heart using two conventional techniques used in cardiac surgery. Using the first technique, the leads 10 were passed through the pericardium and anchor 35 was implanted into the myocardium of the right ventricle. Using the second technique, the anchors 35 of leads 10 were implanted into the myocardium of the left ventricle after the pericardium was excised.

The implanted leads 10 were removed by clamping the proximal ends 22 in an Instron ® tensile tester and applying a steady upward force. The removal force as a function of time was recorded. The peak removal force was used for comparison. Test results are listed in the Table.

TABLE

| Identification Number | Amplitude (mils) | Frequency (cycles per in) | Removal Force (grams) |
| --- | --- | --- | --- |
| 48.5.1 a | 37 | 9 | 362.2 |
| 48.3.1 a | 44 | 9 | 498.1 |
| 48.0.1 a | 50 | 9 | 679.2 |
| 30.17.2 a | 26 | 7 | 127.4 |
| 30.17.1 a | 26 | 7 | 172.6 |
| 30.12.1 a | 51 | 7 | 407.5 |
| 30.7.2 a | 63 | 7 | 452.8 |
| 30.7.1 a | 63 | 7 | 430.2 |
| 48.5.2 b | 37 | 9 | 82.1 |
| 48.5.3 b | 37 | 9 | 152.8 |
| 48.3.3 b | 44 | 9 | 62.3 |
| 48.3.2 b | 44 | 9 | 288.7 |
| 48.0.2 b | 50 | 9 | 308.5 |
| 48.0.3 b | 50 | 9 | 370.7 |
| 30.17.3 b | 26 | 7 | 17.0 |
| 30.12.3 b | 51 | 7 | 243.4 |
| 30.12.2 b | 51 | 7 | 172.6 |
| 30.7.3 b | 63 | 7 | 99.1 |

Note:
a = implanted through pericardium
b = pericardium excised

The peak removal force of the pacing leads 10 of the present invention varies as a function of the amplitude and frequency of the anchor shape. Typical anchor shapes are illustrated in FIGS. 7A–7F. In this example, the anchors with the higher frequency had higher peak removal force values for a given amplitude. As amplitude increased, the force to remove also increased. The amplitude and frequency of the anchors for each test run is listed in the Table.

EXAMPLE 2

A mammal is prepared for cardiac surgery using conventional surgical preparatory techniques. The surgeon then enters the patient's chest cavity by cutting through the sternum and expanding the rib cage with a chest expander. A conventional cardiac bypass surgical procedure is then performed. At the conclusion of the surgical procedure, the surgeon implants a cardiac pacing lead 10 by inserting the needle 40 through the pericardium into the myocardium of the left ventricle. The needle 40 is pulled with a conventional needle holder through the myocardium until the anchor 35 is set in place in the pathway formed by needle 40. The needle 40 is then cut off from the distal end 24 of wire 20 and removed from the thoracic cavity. The surgeon then pushes the electrode needle 60, having score line 68, through the patient's chest wall in between an intercostal space so that the point 62 of the needle protrudes through the chest wall of the patient. The surgeon then grasps the end 63 of the needle 60 with a conventional needle grasper and pulls the needle 60 and the length of the wire 20 through the chest wall. The surgeon then breaks the proximal end 63 off of the electrode needle 60 adjacent to the score line 68 and inserts the electrode 70 into a conventional cardiac pacing/monitoring device 80 such as a Dual-Chamber External Pacemaker Model 3070 manufactured by Pacesetter Systems, Inc., Sylmar, Calif. or equivalents thereof. The patient's heart is monitored and paced by the instrument 80 through the cardiac pacing lead 10. The wire 20 has a hand similar to conventional sutures. The pacing lead 10 remains in the patient during a recuperation period. The anchor 35 effectively holds the conductive section 30 in the myocardium. Tissue ingrowth is minimized.

When the patient has recovered such that pacing and monitoring is no longer necessary, the pacing lead 10 is removed by disconnecting the electrode 70 from the pacing/monitoring instrument 80 and the proximal end of the wire 20 is grasped and pulled outwardly by the surgeon such that the wire 40 and the anchor 35 are withdrawn from the cardiac muscle and out through the chest wall of the patient. Removal of the pacing lead 10 is facilitated by minimal tissue ingrowth.

The cardiac pacing leads 10 of the present invention have many advantages. The low modulus wire 20 is a single filament but has the "hand" of a conventional multi-filament wire without the disadvantages attendant with a multi-filament wire. The lead 10 is easier to manufacture than multifilament pacing leads but yet has the required electrical and mechanical properties. The integral anchor 35 formed into the lead 10 provides anchoring without the need for either suturing or additional anchor elements. In addition, the lead 10 having a single filament wire 20 minimizes or eliminates tissue infiltration associated with multi-filament pacing leads.

Although this invention has been shown and described with respect to detailed embodiments thereof, it will be understood by those skilled in the art that various changes in form and detail thereof may be made without the parting from the spirit and scope of the claimed invention.

What is claimed is

1. A cardiac pacing lead, comprising:
conductive wire means comprising a single filament of a low modulus, biocompatible metal having a modulus of elasticity less than about 2,000,000 psi, said wire means having a proximal end and a distal end; anchor means formed into the distal end of said wire means effective to anchor the pacing lead in the heart of a mammal;
surgical needle means attached to the distal end of said wire means; and
electrode means conductively attached to the proximal end of said wire means.

2. The cardiac pacing lead of claim 1 wherein the conductive wire means is at least partially coated with an electrically insulating material and the distal end of the wire is uncoated.

3. The cardiac pacing lead of claim 1 wherein the surgical needle means comprises a curved surgical needle having a distal piercing point and a proximal cavity for receiving the distal end of the wire means.

4. The cardiac pacing lead of claim 1 wherein the electrode means comprises an electrode needle, the electrode needle comprising a piercing point on one end and a cavity on the other end for receiving the proximal end of the conductive wire means.

5. The cardiac pacing lead of claim 4 wherein the electrode needle further comprises score means such that the piercing point of the needle may be broken away from the body of the needle.

6. The cardiac pacing lead of claim 1, wherein the anchor means comprises a wave configuration formed into the distal end of the wire .

7. The cardiac pacing lead of claim 1 wherein the metal comprises Nitinol.

8. The cardiac pacing lead of claim 6 wherein the wave configuration comprises a square wave.

9. The cardiac pacing lead of claim 6 wherein the wave configuration comprises a sine wave.

10. The cardiac pacing lead of claim 6, wherein the wave configuration is a gear wave.

11. The cardiac pacing lead of claim 1 wherein the conductive wire means comprises a single filament of a low modulus biocompatible metal having a modulus of elasticity of about $1.0 \times 10^6$ psi to about $2.0 \times 10^6$ psi.

12. A cardiac pacing wire, comprising:
conductive wire means comprising a single filament of a low modulus, biocompatible metal having a modulus of elasticity less than about 2,000,000 psi, said wire means having a proximal end and a distal end; and,
anchor means formed into the distal end of said wire means effective to anchor the pacing lead in the heart of a mammal.

13. The cardiac pacing lead of claim 12 wherein the conductive wire means is at least partially coated with an electrically insulating material and the distal end of the wire is uncoated.

14. The cardiac pacing lead of claim 12, wherein the anchor means comprises a wave configuration formed into the distal end of the wire .

15. The cardiac pacing lead of claim 12 wherein the metal comprises Nitinol.

16. The cardiac pacing lead of claim 14 wherein the wave configuration comprises a square wave.

17. The cardiac pacing lead of claim 14 wherein the wave configuration comprises a sine wave.

18. The cardiac pacing lead of claim 14, wherein the wave configuration is a gear wave.

19. The cardiac pacing lead of claim 12 wherein the conductive wire means comprises a single filament of a low modulus biocompatible metal having a modulus of elasticity of about $1.0 \times 10^6$ psi to about $2.0 \times 10^6$ psi.

20. A method of cardiac pacing or monitoring using a cardiac pacing lead, the lead comprising:
conductive wire means comprising a single filament of a low modulus, biocompatible metal having a modulus of elasticity less than about 2,000,000 psi, said wire means having a proximal end and a distal end; anchor means formed into the distal end of said wire means effective to anchor the pacing lead in the heart of a mammal;
surgical needle means attached to the distal end of said wire means; and
electrode means conductively attached to the proximal end of said wire means,
wherein the method comprises:
inserting the surgical needle and at least a section of the anchor means into the heart of a mammal;
removing the surgical needle;
inserting the electrode means into a pacing and monitoring apparatus; and,
monitoring and pacing the heart.

21. The method of claim 20 wherein the conductive wire means is at least partially coated with an electrically insulating material and the distal end of the wire is uncoated.

22. The method of claim 20 wherein the surgical needle means comprises a curved surgical needle having a distal piercing point and a proximal cavity for receiving the distal end of the wire means.

23. The method of claim 20 wherein the electrode means comprises an electrode needle, the electrode needle comprising a piercing point on one end and a cavity on the other end for receiving the proximal end of the conductive wire means.

24. The method of claim 23 wherein the electrode needle further comprises score means such that the piercing point of the needle may be broken away from the body of the needle.

25. The method claim 20, wherein the anchor means comprises a wave configuration formed into the distal end of the wire.

26. The method of claim 20 wherein the metal comprises Nitinol.

27. The method of claim 25 wherein the wave configuration comprises a square wave.

28. The method claim 25 wherein the wave configuration comprises a sine wave.

29. The method of claim 25, wherein the wave configuration is a gear wave.

30. The method of claim 20 wherein the conductive wire means comprises a single filament of a low modulus biocompatible metal having a modulus of elasticity of about $1.0 \times 10^6$ psi to about $1.6 \times 10^6$ psi.

31. A cardiac pacing lead, comprising:
conductive wire means comprising a single filament of a low modulus, biocompatible metal having a modulus of elasticity less than about 2,000,000 psi, said wire means having a proximal end and a distal end, wherein the conductive wire means is at least partially coated with an electrically insulating material and the distal end of the wire is uncoated;
anchor means formed into the distal end of said wire means effective to anchor the pacing lead in the heart of a mammal;
surgical needle means attached to the distal end of said wire means wherein the surgical needle means comprises a curved surgical needle having a distal piercing point and a proximal cavity for receiving the distal end of the wire means; and
electrode means conductively attached to the proximal end of said wire means wherein the electrode means comprises an electrode needle, the electrode needle comprising a piercing point on one end and a cavity on the other end for receiving the proximal end of the conductive wire means and wherein the electrode needle further comprises score means such that the piercing point of the needle may be broken away from the body of the needle.

32. The cardiac pacing lead of claim 31, wherein the anchor means comprises a wave configuration formed into the distal end of the wire.

33. The cardiac pacing lead of claim 32, wherein the wave configuration comprises a square wave.

34. The cardiac pacing lead of claim 32, wherein the wave configuration comprises a sine wave.

35. The cardiac pacing of claim 32, wherein the wave configuration is a gear wave.

36. The cardiac pacing lead of claim 31, wherein the metal comprises Nitinol.

37. The cardiac pacing lead of claim 31, wherein the conductive wire means comprises a single filament of a low modulus biocompatible metal having a modulus of elasticity of about $1.0 \times 10^6$ psi to about $2.0 \times 10^6$ psi.

38. A method of cardiac pacing or monitoring using a cardiac pacing lead, the lead comprising
conductive wire means comprising a single filament of a low modulus, biocompatible metal having a modulus of elasticity less than about 2,000,000 psi, said wire means having a proximal end and a distal end, wherein the conductive wire means is at least partially coated with an electrically insulating material and the distal end of the wire is uncoated;

anchor means formed into the distal end of said wire means effective to anchor the pacing lead in the heart of a mammal;

surgical needle means attached to the distal end of said wire means wherein the surgical needle means comprises a curved surgical needle having a distal piercing point and a proximal cavity for receiving the distal end of the wire means; and electrode means conductively attached to the proximal end of said wire means wherein the electrode means comprises an electrode needle, the electrode needle comprising a piercing point on one end and a cavity on the other end for receiving the proximal end of the conductive wire means and wherein the electrode needle further comprises score means such that the piercing point of the needle may be broken away from the body of the needle.

wherein the method comprises:

inserting the surgical needle and at least a section of the anchor means into the heart of a mammal;

removing the surgical needle;

inserting the electrode means into a pacing and monitoring apparatus; and, monitoring and pacing the heart.

39. The method claim 38, wherein the anchor means comprises a wave configuration formed into the distal end of the wire.

40. The method of claim 38, wherein the metal comprises Nitinol.

41. The method of claim 38, wherein the wave configuration comprises a square wave.

42. The method claim 38, wherein the wave configuration comprises a sine wave.

43. The method of claim 38, wherein the wave configuration is a gear wave.

44. The method of claim 38 wherein the conductive wire means comprises a single filament of low modulus biocompatible metal having a modulus of elasticity of about $1.0 \times 10^6$ to about $1.6 \times 10^6$ psi.

* * * * *